(12) United States Patent
Butler et al.

(10) Patent No.: US 9,101,721 B2
(45) Date of Patent: Aug. 11, 2015

(54) DOSE SETTING MECHANISM AND METHOD OF SETTING A DOSE

(75) Inventors: Joseph Butler, Warwickshire (GB); David Plumptre, Worcestershire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/878,555

(22) PCT Filed: Oct. 11, 2011

(86) PCT No.: PCT/EP2011/067681
§ 371 (c)(1),
(2), (4) Date: Apr. 9, 2013

(87) PCT Pub. No.: WO2012/049144
PCT Pub. Date: Apr. 19, 2012

(65) Prior Publication Data
US 2013/0197479 A1 Aug. 1, 2013

Related U.S. Application Data

(60) Provisional application No. 61/392,760, filed on Oct. 13, 2010.

(30) Foreign Application Priority Data

May 31, 2011 (EP) .................................... 11168194

(51) Int. Cl.
*A61M 5/315* (2006.01)
*A61M 5/31* (2006.01)

(52) U.S. Cl.
CPC ....... *A61M 5/31535* (2013.01); *A61M 5/31525* (2013.01); *A61M 5/31551* (2013.01); *A61M 5/31585* (2013.01); *A61M 5/3146* (2013.01); *A61M 2005/3126* (2013.01)

(58) Field of Classification Search
CPC .......... A61M 5/31551; A61M 5/3158; A61M 5/31585; A61M 5/3156; A61M 5/31541; A61M 5/31593; A61M 5/31525; A61M 5/31555; A61M 5/31561; A61M 5/31575; A61M 5/31595; A61M 5/31563; A61M 5/3155; A61M 5/31583; A61M 5/31501; A61M 5/31533; A61M 5/31548
See application file for complete search history.

(56) References Cited

U.S. PATENT DOCUMENTS 5,626,566 A * 5/1997 Petersen et al. ............... 604/208
6,221,053 B1 4/2001 Walters et al.
(Continued)

FOREIGN PATENT DOCUMENTS

CN 1780652 5/2006
(Continued)

OTHER PUBLICATIONS

Form PCT/IB/326, Notification Concerning Transmittal of International Preliminary Report on Patentability.
(Continued)

*Primary Examiner* — Rebecca E Eisenberg
*Assistant Examiner* — Weng Lee
(74) *Attorney, Agent, or Firm* — McDonnell Boehnen Hulbert & Berghoff LLP

(57) ABSTRACT

A method and system for preventing delivery of less than a predetermined minimum dose of a medicament by providing a dose setting mechanism having a spindle nut and a sprung lock nut. The mechanism includes a housing and a dose dial component positioned in the housing. The dose dial component is rotatable during a dose setting step. The mechanism further includes a drive sleeve positioned within the dose dial component. The drive sleeve is configured to drive a rotatable spindle during a dose administration step. The spindle nut is coupled to the spindle and the sprung lock nut is removably coupled to the drive sleeve and rotationally fixed to the housing. In one arrangement, when the dose dial component is rotated to select a dose less than a preselected minimum dose, the sprung lock nut allows the spindle nut to rotate thereby preventing the dose from being administered.

18 Claims, 4 Drawing Sheets

(56) References Cited

U.S. PATENT DOCUMENTS 7,695,454 B2 * 4/2010 Barron et al. .......... 604/207
8,679,069 B2   3/2014 Veasey et al.

FOREIGN PATENT DOCUMENTS

| WO | 2004078239 | A1 | 9/2004 |
| WO | 2005018721 | A1 | 3/2005 |
| WO | 2006086983 | A1 | 8/2006 |

OTHER PUBLICATIONS

Chinese Office Action for CN App. No. 201180049816.8, dated Jul. 28, 2014.

* cited by examiner

DOSE SETTING MECHANISM AND METHOD OF SETTING A DOSE

CROSS REFERENCE TO RELATED APPLICATIONS

The present application is a U.S. National Phase Application pursuant to 35 U.S.C. §371 of International Application No. PCT/EP2011/067681 filed Oct. 11, 2011, which claims priority to U.S. Provisional Patent Application No. 61/392,360 filed on Oct. 13, 2011 and European Patent Application No. 11168194.6 filed May 31, 2011. The entire disclosure contents of these applications are herewith incorporated by reference into the present application.

FIELD OF INVENTION

The present patent application is generally directed to dose setting mechanisms for drug delivery devices that control minimum and/or maximum possible dose settings and a method of setting and delivering at least a predetermined minimum dose of a medicament. More particularly, the present patent application is generally directed to drug delivery devices, such as pen type drug delivery devices where therapy demands that a patient receive at least a certain minimum dose and not exceed a certain maximum dose of a particular medicament. Such devices provide for self-administration of medicinal product from a multi-dose cartridge and contain dose limiting mechanisms for setting minimum and/or maximum doses. The present application may find application in both disposable and reusable type drug delivery devices. However, aspects of the invention may be equally applicable in other scenarios as well.

BACKGROUND

Self administered injectable medicaments are often delivered using a variable-dose injection device. Such a device is known from WO 2004/078239 A1. Prior to the injection the user selects the dose that they require according to their prescribed dose and/or their current or expected future physical condition. A typical example would be an insulin delivery device for diabetics where a patient's dose is determined according to their prescribed dose and their expected food intake and activity level. Typically such devices allow the user to select any dose from 1 unit up to the maximum units that the device can deliver, typically 60 units or 80 units for a manual device, such as a pen-type or syringe injection device.

The drug delivery device of WO 2004/078239 A1 comprises a housing for receiving a dose setting mechanism, a cartridge, a dose dial sleeve with an attached dose dial grip, a clicker, a drive sleeve, a clutch for coupling and decoupling the dose dial sleeve and the drive sleeve, a rotatable piston rod and a button which is pressed for injecting a set dose. The full description of the pen-type injection devices disclosed in WO 2004/078239 A1 is incorporated herein by reference.

To dial a dose a user rotates the dose dial grip. With the clicker and clutch means engaged, the drive sleeve, the clicker, the clutch means and the dose dial sleeve rotate with the dose dial grip relative to the housing and relative to the piston rod. Audible and tactile feedback of the dose being dialed is provided by the clicker and the clutch means. Torque is transmitted through saw teeth between the clicker and the clutch means.

A helical groove on the dose dial sleeve and a helical groove in the drive sleeve have the same lead. This allows the dose dial sleeve to extend from the housing and the drive sleeve to climb the piston rod at the same rate. At the limit of travel, a radial stop on the dose dial sleeve engages a stop provided on the housing to prevent further movement. Rotation of the piston rod is prevented due to the opposing directions of overhauled and driven threads on the piston rod.

Should a user inadvertently dial beyond the desired dosage, the pen-type injector allows the dosage to be dialed down without dispense of medicinal product from the cartridge. The dose dial grip is counter rotated. This causes the system to act in reverse. The torque transmitted through the clutch means causes the saw teeth to ride over one another to create the clicks corresponding to dialed dose reduction. Preferably the saw teeth are so disposed that the circumferential extent of each saw tooth corresponds to a unit dose.

When the desired dose has been dialed, the user may then dispense this dose by depressing the button. This displaces the clutch means axially with respect to the dose dial sleeve causing dog teeth of the clutch means to disengage. However the clutch means remains keyed in rotation to the drive sleeve. The dose dial sleeve and associated dose dial grip are now free to rotate. The axial movement deforms a flexible part of the clicker to ensure the saw teeth cannot be overhauled during dispense. This prevents the drive sleeve from rotating with respect to the housing though it is still free to move axially with respect thereto. This deformation is subsequently used to urge the clicker and the clutch back along the drive sleeve to restore the connection between the clutch and the dose dial sleeve when pressure is removed from the button. The longitudinal axial movement of the drive sleeve causes the threaded piston rod to rotate through a threaded opening in a housing insert, thereby to advance the piston in the cartridge.

In other words, the drive sleeve moves longitudinally, i.e. only in the axial direction, during an injection. Because the drive sleeve and the piston rod are engaged via corresponding threads on the outer surface of the piston rod and an internal face of the drive sleeve, the longitudinal movement of the drive sleeve causes the piston rod to rotate. The housing insert with the threaded opening which is engaged with the piston rod via corresponding threads is fixed within the housing, i.e. prevented from rotation. Thus, the rotating piston rod is screwed through the threaded opening in the housing insert, i.e. the piston rod performs a combined rotational and longitudinal movement along a helical path defined by the corresponding threads of the threaded opening and the piston rod.

Once the dialed dose has been dispensed, the dose dial sleeve is prevented from further rotation by contact of a plurality of members extending from the dose dial grip with a corresponding plurality of stops formed in the housing, thus determining a zero dose position.

Such pen type drug delivery devices have been designed and developed to perform regular injections by persons without formal medical training. This is increasingly common among patients having diabetes where self-treatment enables such patients to conduct effective management of their disease. Because the patient, and not the health care worker, may be using such a drug delivery device, one requirement is that the device should be robust in construction. The drug delivery device must also be easy to use both in terms of the drug delivery device manipulation and understanding of the device's operation. This is especially true for diabetics who are required to inject themselves repeatedly with insulin solution and the volume of insulin to be injected may vary from patient to patient and even from injection to injection. For at least this reason, certain diabetics may require drug delivery devices that allow the patient to inject successive measured dosages of the same or perhaps different preset volumes of insulin solution accurately and with minimum dexterity challenges. This presents a further design challenge since, in the case of certain diabetics, users may have impaired vision and/or may be physically infirm with limited dexterity.

In addition to insulin, other medicaments require a minimum dose to be delivered before they are therapeutically effective. A variable-dose device that allows the patient to deliver doses below the therapeutically effective minimum dose creates the possibility that the user may deliver the ineffective doses either by an error of dose calculation or by mistakenly selecting the incorrect dose. Likewise, some medicaments require that a maximum dose is not to be exceeded. This may be for safety reasons such as increased risk or severity of side-effects or excessive or unwanted actions of the medicament. Current variable-dose delivery devices typically have a maximum dose that is limited by the maximum dose that the delivery mechanism can provide, however, this does not necessarily relate to the maximum advised or prescribed dose of the medicament.

SUMMARY

It is an object of the invention to provide a device that reduces or eliminates the risk that a user of an injection device will set and administer a dose below a preselected minimum effective dose of a particular medicament.

This object is solved with a dose setting mechanism as defined in claim 1. The present invention has at least two applications. First, is the delivery of a single active medicament which must be a variable dose within a defined dose window, i.e. the dose must be more than a certain minimum dose and must not exceed a certain maximum dose. The second application relates to the delivery of a combined formulation of active medicaments where at least one of the medicaments is preferably delivered as a variable dose and at least one other medicament is preferably delivered as a fixed dose, and where this fixed dose can safely be allowed to vary within a defined dose window, for example by ±10% of the nominal fixed dose.

The minimum and/or maximum dose limited delivery device in accordance with our disclosure could be used for a medicament that requires a minimum dose to be delivered before it becomes therapeutically effective, but where a degree of dose adjustment may be required. This dose adjustment may be required for a number of reasons, including tailoring a dose to a patient's body weight or the severity of their medical condition. The minimum and maximum dose limited device (min/max device) may also be used instead of a fully variable (i.e., 0 to max dose) device in order to reduce the possibility for dosing errors by the patient. Using the min/max device rather than a variable dose pen reduces the risk that a patient might accidentally deliver a dose outside the defined dose window, i.e., either too high or too low.

One example of the utility of the min/max device is where a parent could give the min/max delivery device to a child for the child to self-administer and the parent would know that the minimum and maximum levels of the min/max device limited the possible severity of any overdose or under dose. Another example of where such a device might be applicable is for patients who take long acting insulin. Typically a variable dose pen is required when a patient is "titrating" their dose to reach their target blood glucose level. However, once the target blood glucose level has been achieved the dose of long acting insulin typically remains more or less constant over relatively long periods of time. During this period, where their insulin dose is either constant or changes by only a few units on a day-to-day basis, the patient's long acting insulin needs could be effectively met by the minimum and maximum dose limited delivery device.

Table 1 (provided below) shows an example family of delivery devices, "Pen 1" through "Pen 4", which could be used in place of a single 1-80 unit variable dose device. Each of the Pens 1-4 are designed and manufactured around the same basic mechanism, but each pen contains either additional or alternative components which are used to set a different minimum and maximum dose. Patients would be prescribed a particular Pen according to their stable long acting insulin dose. For example, according to Table 1 a patient prescribed 30 units per day of long acting insulin would be prescribed Pen 2, which has a minimum dose of 18 units and a maximum dose of 42 units, respectively. Any number of mechanical components can be used in such a pen design to ensure these predetermined min/max doses, including axial and/or rotational stops, detents, clutches, compressible fingers, or the like components. In an example, a sprung lock nut and a spindle nut may be configured to ensure these predetermined min/max doses.

The insulin dose of diabetic patients may change gradually over time. Therefore there may be a small amount of dose range overlap between Pens to allow for a smooth transition between Pens as the dose increases. For example, according to Table 1 a patient prescribed 40 units per day of long acting insulin would be given Pen 2 if they expected their dose to decrease over time or Pen 3 if they expected their dose to increase over time. The number of pens in the "family" and the selected dose ranges shown in Table 1 are illustrative only. By using the min/max device of the present invention a mistake when selecting the dose is limited to within the pen's operating window. Dialing a dose above or delivering a dose below the pen's dose range would not be possible and this would alert the patient to their error.

The min/max device may also be applicable for the delivery of other medicines, particularly where there is a risk of confusion with similar devices that may lead to dose errors or drug/device mix-ups. One such example would be rapid acting insulin and long acting insulin. Both of these insulins are measured in "units" however the same number of units of each insulin type will have a very different effect and a patient will be prescribed different doses of each drug to be taken at different times throughout the day. A mix up of long acting and rapid acting insulin can cause hypoglycemia and is potentially fatal. Both types of insulin may be delivered by injection pen devices. Patients perform their injections on such a routine basis that an "automatic pilot" effect can occur where patients have been known to mix up their insulin pens, even though the pens are of different design, color, shape and carry different labels.

The presently proposed min/max device may help to prevent this mix up occurring. For example, assume both rapid acting and long acting insulins were each provided with a family of min/max devices according to Table 1. A patient is prescribed 50 units per day of long acting insulin (which would require long acting Pen 3) and 15 units of rapid acting insulin with meals (which would require Pen 1). The most dangerous mix up would occur if the patient mistakenly delivered 50 units of rapid acting insulin rather than long acting insulin. If the patient attempted to do this with the min/max devices then the patient would pick up the rapid insulin device (Pen 1) and find that they could not dial beyond 22 units. This should alert them to the fact that this is not the correct insulin pen, and therefore the incorrect insulin type, and prevent the incorrect insulin being delivered.

The min/max concepts may be applied equally to both disposable devices and reusable devices.

Certain medicines also require the user to perform a "priming" dose to confirm the correct operation of the delivery device and needle. This is usually accomplished by delivering an "air-shot" of 2 units and then checking that the medicine can be seen coming out of the needle. The min/max concept shown in Table 1 would not permit this. If priming functionality is required a second permissible "dose window", for example ranging from 1-2 units, may also be implemented within each pen mechanism. An example of how this could be applied is shown in Table 2. Although both Tables 1 and 2 show only even numbers of units this is done only for clarity and the device may be configured to deliver odd and even units or potential ½ units.

As mentioned, the presently disclosed devices may also be useful in therapies where the delivery of a combined formulation of active medicaments is needed, where at least one of the medicaments is preferably delivered as a variable dose and at least one other medicament is preferably delivered as a fixed dose. If a patient requires a combination of medicines then there is an advantage if those medicines can be provided as a single formulation (i.e. both drugs are mixed together in predefined proportions and supplied in one primary pack) for delivery by a single injection device in one injection through a single needle. However, if one of the drugs requires the delivery of a user-selectable variable dose and the second drug requires a dose above a minimum dose to be therapeutically effective and must not exceed a given maximum dose, then it is beneficial for the drug delivery device to be configured such that it is prevented from delivering doses that are outside of this range.

For example, a patient may be prescribed a combination therapy of long acting insulin (typically delivered in variable dose devices) and GLP-1 (typically delivered as a fixed dose). GLP-1 is a glucagon-like peptide-1, which is derived from the transcription product of the proglucagon gene and is found in the body where it is secreted by the intestinal L cell as a gut hormone. GLP-1 possesses several physiological properties that make it (and its analogs) a subject of intensive investigation as a potential treatment of diabetes mellitus. In order to avoid the patient having to perform two injections the two medicines are pre-mixed into a single formulation. Since both medicaments are pre-mixed in a fixed ratio it is not possible to vary the long acting insulin dose without also varying the GLP-1 dose. However, it may be acceptable for the GLP-1 dose to vary within a given tolerance, for example ±10%, around a fixed nominal dose. It is therefore possible, using a family of min/max limited devices to provide a family of pre-mix devices which between them will allow delivery of a variable long acting insulin dose and a GLP-1 dose that always falls within ±10% of a given "fixed" dose.

Table 3, for example, shows a family of 6 min/max pen-type injection devices that allow the delivery of any long acting insulin dose from 22-76 units along with a GLP-1 dose that is "fixed" to 20 mg±10%. Each Pen within the family would have different minimum and maximum dose thresholds and would be provided with a primary pack or cartridge of medicament filled with the appropriate mix ratio of the two medicines. The family of pen devices could be provided as disposable mechanical devices, prefilled with the appropriate mix ratio cartridge of medicament. Alternatively, the family of devices could be provided as reusable mechanical devices. In the latter case, the devices would be preferably dedicated to a particular mix ratio cartridge, i.e. only the correct mix ratio cartridge can be loaded into each pen family member.

A third alternative is to provide the "family" of pen devices via a single electronic device that can be programmed with the minimum and maximum dose functionality. Preferably, the min/max electronic device would be loaded with a coded cartridge that would automatically upon being loaded into the device communicate to the device what the required minimum and maximum thresholds should be for that particular cartridge and mix ratio.

One specific means of achieving a minimum settable dose on a variable dose, drug delivery device, such as a pen-type device, is to include a mechanism that prevents dosing of the device until a predetermined minimum dose has been reached. A maximum dose mechanism can also be used with a minimum dose mechanism.

The minimum dose limiting function as disclosed herein may be achieved by means of a spindle nut and a sprung lock nut. According to one possible exemplary embodiment, a dose setting mechanism for a drug delivery device is provided comprising a drug delivery device housing, a dose dial component positioned at least partly in the housing, and a drive sleeve positioned at least partly within the dose dial component. The dose dial component is rotatable during a dosing step, and the drive sleeve is configured to drive a rotatable spindle during a dose administration step. The dose setting mechanism also includes a spindle nut coupled to the spindle and a sprung lock nut releasably coupled to the drive sleeve and rotationally fixed to the housing. If the dose dial component is rotated to select a dose less than a preselected minimum dose and dose delivery is attempted the sprung lock nut will allow the spindle nut to rotate thereby preventing the dose from being administered since the piston rod will not be forced to advance. In other words, the spindle nut has a function similar to that of the threaded opening in the housing insert of the above mentioned device according to WO 2004/078239 A1. However, in contrast to the threaded opening in a housing insert the spindle nut may rotate depending on the position of and/or engagement with the sprung lock nut, thus either allowing (with the spindle nut keyed to the housing via the sprung lock nut) or preventing (with the spindle nut not keyed to the housing via the sprung lock nut) a dose from being administered.

According to the present invention it is preferred to design and arrange the spindle nut and the sprung lock nut such that, when the dose dial component is rotated to select a dose greater than a preselected first dose and less than a preselected second dose, the sprung lock nut is decoupled from the spindle nut thus allowing the spindle nut to rotate thereby preventing the selected dose from being administered. The predetermined first dose and the predetermined second dose may be chosen according to the individual needs of different groups of users. For example, the predetermined first dose may be zero units, thus preventing any dose being less than the preselected second dose (minimum dose) from being administered. As an alternative, the predetermined first dose may be more than zero units, e.g. a priming dose of 1 or 2 units. In the latter case, a priming step can still be performed by the user, however injection of a dose greater than the preselected first dose (priming dose) and less than the preselected second dose (minimum dose) is prevented.

In another example, a method of delivering at least a predetermined minimum dose of a medicament is provided. The method includes setting a dose by rotating a dose dial component in a first direction relative to a device housing, where the dose dial component is in clutched engagement with a drive sleeve causing the drive sleeve to rotate with the dose dial component, the dose dial component and the drive sleeve moving in a proximal axial direction, wherein the drive sleeve is configured to rotationally drive a spindle during a dose administration step. Further, the method includes forcing a sprung lock nut to disengage from a spindle nut at the time the user set a dose equal to or larger than a predefined minimum dose value, wherein the spindle nut is coupled to the spindle and is axially fixed with respect to the housing. Still further, the method includes, at a predetermined distance of the drive sleeve corresponding to the predefined minimum dose value, forcing the sprung lock nut to disengage from the drive sleeve, wherein a biasing member forces the sprung lock nut to reengage with the spindle nut. When the sprung lock nut and the spindle nut are engaged, the sprung lock nut prevents the spindle nut from rotating with respect to the housing. As long as the spindle nut is prevented from rotation, administration of a dose is possible by moving the drive sleeve distally without rotation and thereby advancing the spindle through the spindle nut. Other exemplary methods of delivering at least a predetermined minimum dose of a medicament are possible as well.

In an example of a min/max device, a user can manually override the minimum dose function if required by dialing a dose equal to, or greater than, the predetermined minimum dose and then dialing back down to the required dose level. Additionally, the dose count numbers below the minimum dose may be colored a different color such as red to differentiate that the dose dialed is less than the normal minimum dose.

In another example, an "air shot" or "priming dose" function can be provided by designing the sprung lock nut and the spindle nut to only disengage from one another in axial movement after a certain number of units have been dialed.

These as well as other advantages of various aspects of our proposed drug delivery device will become apparent to those of ordinary skill in the art by reading the following detailed description, with appropriate reference to the accompanying drawings.

BRIEF DESCRIPTION OF THE. DRAWINGS

Exemplary embodiments are described herein with reference to the drawings, in which:

FIG. 1b illustrates a perspective cross-sectional view of the pen-type drug delivery device of FIG. 1a;

DETAILED DESCRIPTION

Figure 1A:
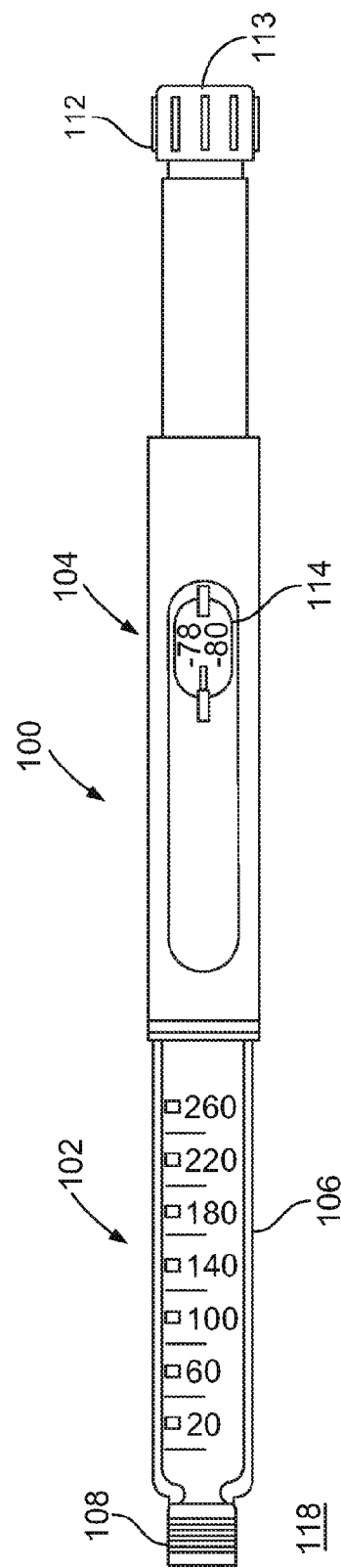
FIG. 1a illustrates an example design of a pen-type drug delivery device.

Referring to FIG. 1a, there is shown a drug delivery device 100 in accordance with an exemplary pen-type design arrangement. The general design and function of the drug delivery device 100 mainly corresponds to that of the device described above with reference to WO 2004/078239 A1.

In more detail, the drug delivery device 100 od the present invention comprises a housing having a first cartridge retaining part 102, and a dose setting mechanism 104. The drug delivery device may be a resettable drug delivery device (i.e., a reusable device) or alternatively a non-resettable drug delivery device (i.e., a non-reusable device). A first end of the cartridge retaining part 102 and a second end of the dose setting mechanism 104 are secured together by connecting features. For non-resettable devices, these connecting features would be permanent and non-reversible. For resettable devices, these connecting features would be releasable.

In this illustrated arrangement, the cartridge retaining part 102 is secured within the second end of the dose setting mechanism 104. A removable cap (not shown) is releasably retained over a second end or distal end of a cartridge retaining part or cartridge housing. The dose setting mechanism 104 comprises a dose dial grip 112 and a window or lens 114. A dose scale arrangement is viewable through the window or lens 114. To set a dose of medication contained within the drug delivery device 100, a user rotates the dose dial grip 112 such that a dialed dose will become viewable in the window or lens 114 by way of the dose scale arrangement.

FIG. 1a illustrates the medical delivery device 100 with the cover cap removed from a distal end 118 of the medical delivery device 100. This removal exposes the cartridge housing 106. Preferably, a cartridge (not shown) from which a number of doses of a medicinal product may be dispensed, is provided in the cartridge housing 106. Preferably, the cartridge contains a type of medicament that can be administered relatively often, such as once or more times a day. One such medicament is either long acting or short acting insulin or an insulin analog; however, any medicament or combination of medicaments is possible. The cartridge comprises a bung or stopper that is retained near a second end or a proximal end of the cartridge. The drug delivery device also comprises a drive sleeve and a spindle (not illustrated in FIG. 1a, but is illustrated as items 124 and 126, respectively, in FIG. 1b).

The cartridge housing 106 has a distal end and a proximal end. Preferably, the distal end of the cartridge housing 106 comprises a hub 108 for attaching a removable needle assembly. However, other needle assembly connection mechanisms could also be used. If the drug delivery device 100 comprises a resettable device, the proximal end of the cartridge housing 106 is removably connected to the dose setting mechanism 104. In one preferred embodiment, cartridge housing proximal end is removably connected to the dose setting mechanism 104 via a bayonet connection. However, as those of ordinary skill in the art will recognize, other types of removable connection methods such as threads, partial threads, ramps and detents, snap locks, snap fits, and luer locks may also be used.

As previously mentioned, the dose setting mechanism 104 of the drug delivery device illustrated in FIG. 1a may be utilized as a reusable drug delivery device (i.e., a drug delivery device that can be reset). Where the drug delivery device 100 comprises a reusable drug delivery device, the cartridge is removable from the cartridge housing 106. The cartridge may be removed from the device 100 without destroying the device 100 by merely having the user disconnect the dose setting mechanism 104 from the cartridge housing 106.

In use, once the cap is removed, a user can attach a suitable needle assembly to the hub 108 provided at the distal end of the cartridge housing 106. Such needle assembly may be, for example, screwed onto a distal end of the cartridge housing 106 or alternatively may be snapped onto this distal end. After use, the replaceable cap may be used to re-cover the cartridge housing 106. Preferably, the outer dimensions of the replaceable cap are similar or identical to the outer dimensions of the dose setting mechanism 104 so as to provide an impression of a unitary whole when the replaceable cap is in position covering the cartridge housing 106 when the device is not in use.

Figure 1B:
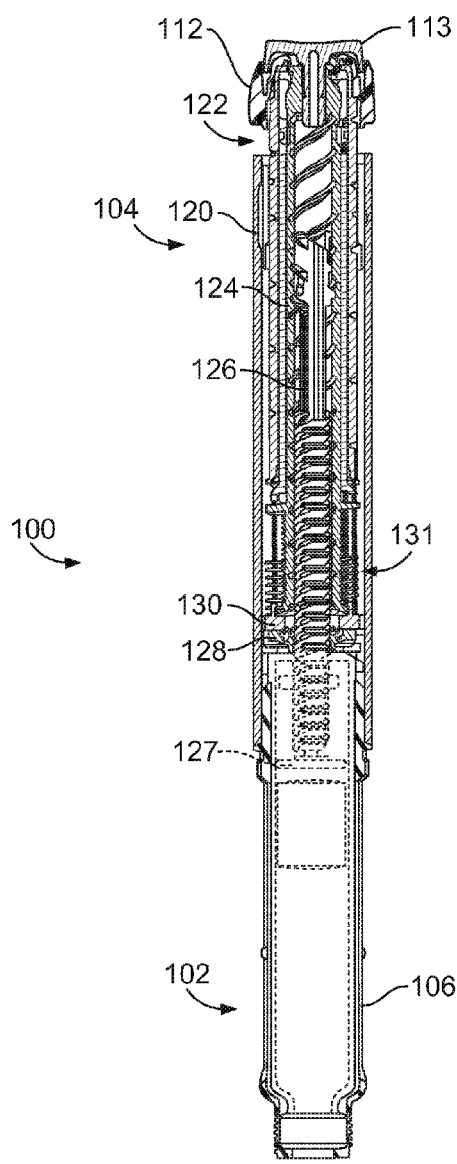

FIG. 1b illustrates a perspective cross-sectional view of drug delivery device 100, and in particular shows a detailed cross-sectional view of dose setting mechanism 104. Dose setting mechanism 104 includes a housing 120 and a dose dial component 122 positioned at least partly in housing 120. The dose dial component is rotatable during a dose setting step. Further, in an example, the dose dial component comprises a number sleeve. The dose setting mechanism 104 also includes a drive sleeve 124 positioned at least partly in the dose dial component 122. This drive sleeve 124 is configured to drive a rotatable spindle 126 during a dose administration step. The dose setting mechanism also includes a spindle nut 128 and a sprung lock nut 130. The spindle nut 128 is coupled to the spindle 126 and is fixed axially with respect to the housing 120. Further, the sprung lock nut 130 is releasably coupled to the drive sleeve 124 and is preferably rotationally fixed to the housing 120. Sprung lock nut 130 is in communication with at least one biasing member. For example, as depicted in FIG. 1b, sprung lock nut 130 is in communication with spring 131.

Figure 2:
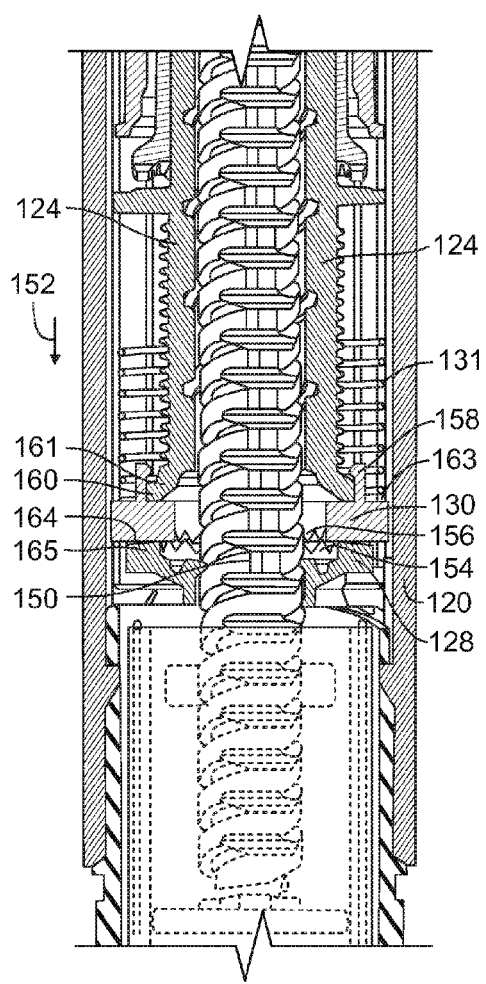
FIG. 2 illustrates a close-up sectional view of the dose setting mechanism shown in FIG. 1b.

In general, when the dose dial component 122 is rotated to select a dose less than a preselected minimum dose, the sprung lock nut 130 allows the spindle nut 128 to rotate, thereby preventing the dose from being administered. With reference to FIG. 2, a distal end 150 of spindle 126 is threadedly connected to spindle nut 128. During an injection step, if the threaded spindle nut 128 is held fixed to the housing 120 (not being allowed to rotate with respect to the housing), when the rotatable spindle 126 is driven by the drive sleeve 124 in a distal direction 152, the spindle 126 will rotate and move axially as it passes through in a thread provided in the spindle nut 128. Therefore the spindle advances forward, and a plunger 127 may provide an axially directed force upon a stopper in a drug cartridge to urge medication from the cartridge through an attached double ended needle mounted on the distal end of cartridge assembly 102. However, when the spindle nut 128 is free to rotate and the spindle 126 is rotated by means of the drive sleeve 124, the spindle nut 128 rotates with the spindle 126 and the spindle is therefore prevented or substantially prevented from applying an axial force on the cartridge, which prevents dispensing of a dose.

As mentioned above, this spindle nut 128 is constrained axially and is free to rotate relative to the housing 120. In a zero dose position (e.g., as illustrated in FIG. 2), the spindle nut 128 is rotationally locked by sprung lock nut 130. Sprung lock nut 130 may be keyed (e.g., splined) to the housing 120 to prevent rotation, but is free to travel axially. Lock nut 130 may be rotationally fixed in other ways, such as being splined to a fixed member (e.g., an insert) that is connected to housing 120. Sprung lock nut 130 may also include protrusions that mate with corresponding similar protrusions on the spindle nut 128 to prevent rotation in a coupled state of the spindle nut 128 and the sprung lock nut 130. In FIG. 2, the spindle nut 128 protrusions and the lock nut 130 protrusions are depicted as teeth 154, 156 respectively. However, it should be understood that protrusions of other types are possible, as well as other means of engaging the spindle nut 128 and lock nut 130. As just one example, in one alternative arrangement, the sprung lock may be rotatable wherein the sprung lock would comprise a thread having a first pitch. This first pitch would be selected such that it is larger than the pitch of the drive sleeve such that when the drive sleeve is rotated to select a dose, the sprung lock 130 also rotates but rotates at a much lower speed and therefore travel a smaller axial distance. For example, in such an arrangement, the first and second pitches may be selected such that if the drive sleeve were rotated 10 revolutions, the sprung lock may rotate once.

The sprung lock nut 130 may include at least one locking arm. For example, lock nut 130 includes locking arm 158, which extends around the full circumference of the lock nut 130. However, in other examples, the locking arm may extend around only a portion of the circumference. This locking arm 158 releasably engages the distal end 160 of drive sleeve 124. When a user rotates the dose dial component 122 so as to set or dial a dose, the drive sleeve 124 rotates helically along with the dose dial component 122, i.e. the drive sleeve 124 performs a combined translational and rotational movement. Therefore, the locking arm 158 provides for the sprung lock nut 130 to travel axially in a proximal direction during initial dose dialing. At a given point corresponding to the minimum dose of drug delivery device 100, as explained in greater detail below, the at least one locking arm 158 disengages from the drive sleeve 124. When the locking arm 158 disengages from the drive sleeve 124, the sprung lock nut 130 returns under the force of spring 131 to its initial position, and this locks the spindle nut 128 against rotation.

The operation of the dose setting mechanism 104 is described in greater detail below with reference to FIGS. 2-5.

First, the operation is described with reference to when a user dials a dose that is less than the minimum dose of the dose setting mechanism 104. As a user rotates the dose dial component 122 to dial a dose, the drive sleeve 124 rotates and travels axially in a proximal direction 162. As illustrated in FIG. 2, the locking arm 158 of the sprung lock nut 130 clip onto a distal portion 160 of the drive sleeve 124. This distal portion 160 may have a corresponding arm 161 extending around the circumference or a portion of the circumference of the drive sleeve. Arm 158 and arm 161 may be clipped together. As such, as the drive sleeve 124 travels in the proximal direction 162, the sprung lock nut 130 travels axially along with the drive sleeve 124. As illustrated, a biasing member or members, such as a spring 131 is provided between a proximal portion 163 of the sprung lock nut 130 and the drive sleeve 124. Moving in the proximal direction 162 during a dose setting step, the sprung lock nut 130 compresses against the spring 131. At the same time, a distal end 164 of the sprung lock nut 130 disengages from a proximal end 165 of the spindle nut 128. In one exemplary arrangement, the design is such that the retention strength of the at least one locking arm 158 is greater than the maximum spring force, and therefore the locking arm 158 will remain engaged to the drive sleeve 124 until a minimum dose value has been selected or dialed by the user.

If a user attempts to deliver a dose that is less than the minimum dose before the minimum dose has been set, then the drive sleeve 124 will travel axially in the distal direction. However, since the sprung lock nut 130 is no longer engaged to the spindle nut 128, the spindle nut 128 is free to rotate and thereby prevents a dose from being delivered. Thus, before dialing a dose greater than the predetermined minimum dose, a user is unable to dispense a dose less than the minimum dose.

Figure 3:
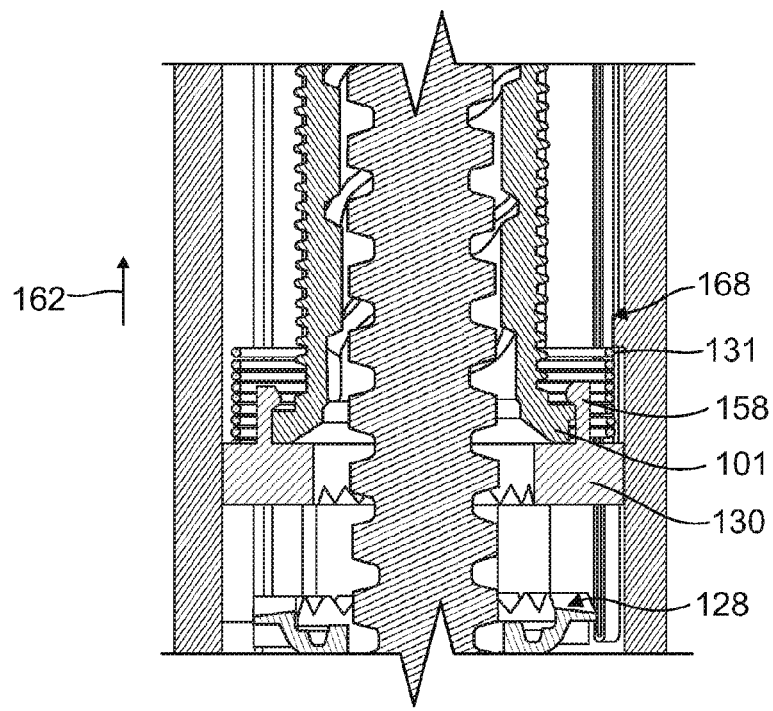
FIG. 3 illustrates a close-up sectional view of the dose setting mechanism shown in FIG. 1b during a dose setting step.

A user may only be able to administer a dose after the user dials a dose that is above the minimum dose of the dose setting mechanism 104. As the dose is dialed, the drive sleeve 124 and sprung lock nut 130 travel in the proximal direction 162 compressing the spring 131. In one example arrangement, an inner wall 166 of the body is provided with a spring stop feature 168, as shown in FIG. 3. The spring geometry and axial position of a spring stop feature shown in FIG. 3 operate to determine the point at which the spring 131 is fully compressed. Generally, this point corresponds to the minimum dose limit, because after this point, any further axial movement in the proximal direction 162 releases the drive sleeve 124 from the lock nut 130.

Figure 4:
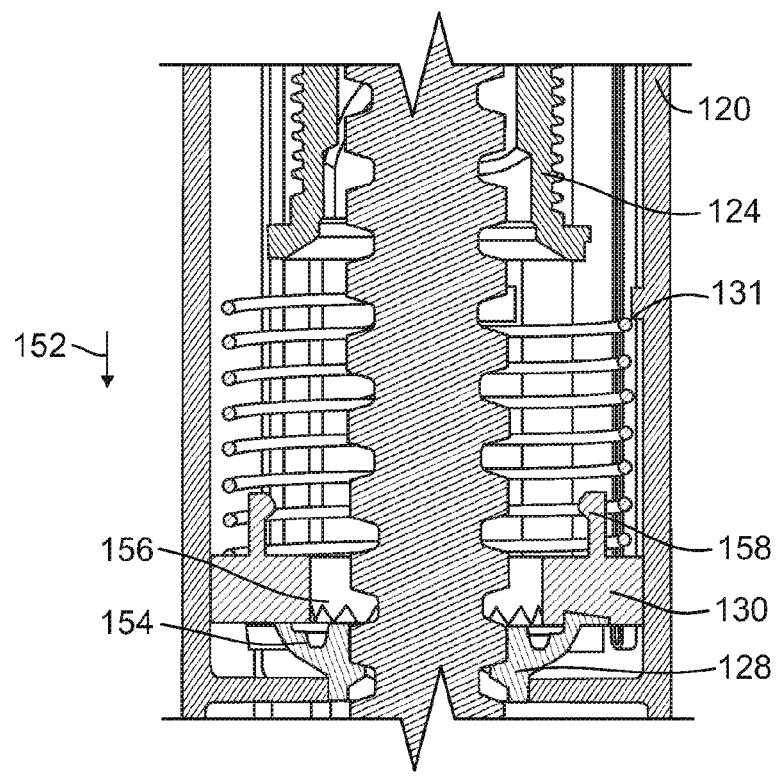
FIG. 4 illustrates a close-up sectional view of the dose setting mechanism shown in FIG. 1b during a dose setting step.
Figure 5:
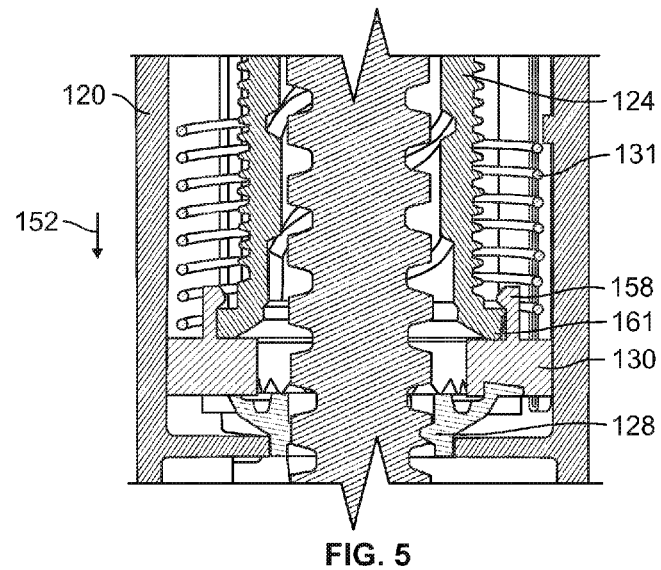
FIG. 5 illustrates a close-up sectional view of the dose setting mechanism shown in FIG. 1b after a dose administration step.

As a dose larger than the minimum dose is dialed, the locking arm 158 of the sprung lock nut 130 disengages from the locking arm 161 of drive sleeve 124. In an example, the locking arm 158 of the sprung lock nut 130 and/or the corresponding locking arm 161 of the drive sleeve 124 may be flexible locking arms, which are capable of flexing when a given force is applied. After the locking arms 158 and 161 disengage from one another, under the force of the compressed spring 131, the sprung lock nut 130 is forced to travel in the distal direction 152. The lock nut 130 returns to its original position, which is illustrated in FIG. 4. In this original position, the distal portion 164 of the sprung lock nut 130 re-engages with the proximal end 165 of the spindle nut 128. As the sprung lock nut 130 is splined to the housing 120, the spindle nut 128 is thereby prevented from rotating. When the spindle nut is prevented from rotating, the user may administer a dose. During a dose administration step, the user may compress a dose button 113, which may drive the drive sleeve 124 in the distal direction 152. An inner thread of the drive sleeve 124 drives the spindle 126 in the distal direction 152 through the spindle nut 128. As the spindle 126 rotates through the spindle nut 128, the dose may be delivered.

During dose delivery, the drive sleeve 124 travels axially in a distal direction 152 driving the spindle 126 and delivering the dose. During the final stages of dose delivery, the locking arm 158 of the sprung lock nut 130 re-engages with the drive sleeve 124. This resets the dose setting mechanism to make the dose setting mechanism ready for the next dose set operation.

As discussed above, a dose can only be delivered if the spindle nut 128 is rotationally locked. In accordance with exemplary arrangements disclosed herein, the minimum dose of a device may be varied by varying when the sprung lock nut 130 disengages from the drive sleeve 124. Therefore, changing the point at which the sprung lock nut 130 is released from the drive sleeve 124—thus re-engaging it with the spindle nut 128 preventing rotation of the said spindle nut 128—will change the minimum dose that must be dialed before it is possible to deliver the dose.

In an example of the min/max device according to the invention, a user can manually override the minimum dose function if required by dialing a dose greater than the minimum dose and then dialing back down to a dose less than the minimum dose. In another example, the dose count numbers below the minimum dose may be coloured a different colour such as red to differentiate that the dose dialed is less than the normal minimum dose. Alternatively, the dose count numbers may not be visible until the minimum dose has been dialed.

Figure 6:
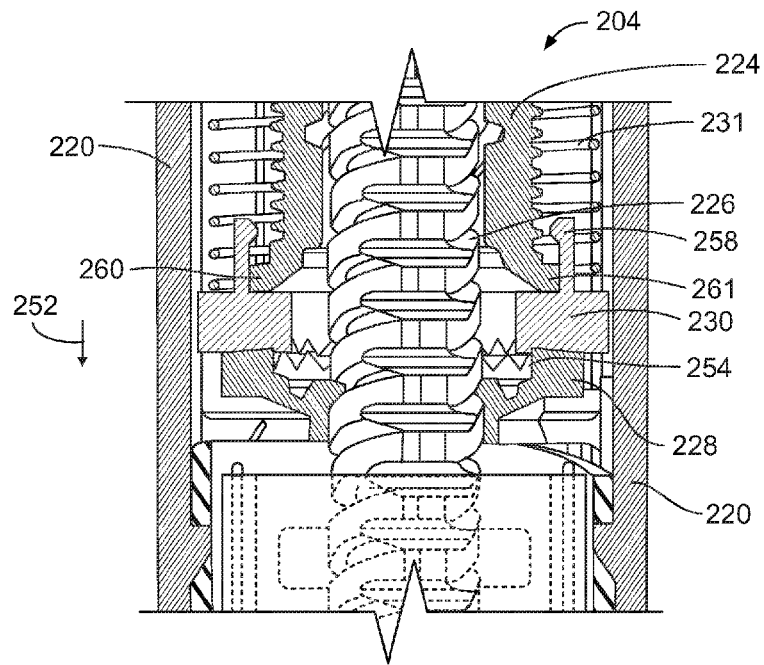
FIG. 6 illustrates a close-up sectional view of an alternative dose setting mechanism that allows a user to perform a priming operation.

In yet another example, the min/max device may be designed to allow a user to perform a priming operation. For example, FIG. 6 illustrates a close-up sectional view of an alternative dose setting mechanism 204 that may be used with a drug delivery device, such as device 100 illustrated in FIG. 1. One difference between dose setting mechanism 104 of FIG. 1 and dose setting mechanism 204 of FIG. 6 is that the alternative mechanism 204 allows a user to perform a predetermined priming operation. Preferably, this dose setting mechanism 204 may be part of a drug delivery device such as a pen type drug delivery device, such as the pen type drug delivery device 100 illustrated in FIG. 1.

Dose setting mechanism 204 operates in a similar fashion as dose setting mechanism 104 and comprises similar components. For example, dose setting mechanism 204 comprises a housing 220 and a dose dial component positioned at least partly in housing 220, similar to the dose dial component 122 previously discussed and illustrated in great detail. The dose dial component is rotatable during a dose setting step. The dose setting mechanism 204 also includes a drive sleeve 224 positioned at least partly in the dose dial component. This drive sleeve 224 is configured to drive a rotatable spindle 226 during a dose administration step. The dose setting mechanism also includes a spindle nut 228 and a sprung lock nut 230 which operate in a similar manner as previously discussed herein. For example, the spindle nut 228 is coupled to the spindle 226 and is fixed axially. Further, the sprung lock nut 230 is removably coupled to the drive sleeve 224 and is rotationally fixed to the housing 220. Sprung lock nut 230 is in communication with at least one biasing member. For example, as depicted in FIG. 6, sprung lock nut 230 is in communication with spring 231.

In this alternative dose setting mechanism 204, when the dose dial component is rotated to select a dose that is greater than a predetermined priming dose and less than a predetermined minimum dose, the sprung lock nut 228 allows the spindle nut 230 to rotate thereby preventing the dose from being administered. The predetermined priming dose may be any suitable dose, such as less than about 4 units, and preferably less than about 2 units. However, when the dose dial component is rotated to select a dose that is less than or equal the predetermined priming dose, the sprung lock nut 228 remains engaged with the spindle nut 230 and thereby prevents rotation of the spindle nut 230. This priming capability could be achieved through the use of a releasable locking arm 258 that engages the drive sleeve locking arm 261 located near the distal end 260 of the drive sleeve 224 only after a predefined priming dose (e.g., 2 units) have been dialed. This predefined priming dose may be defined by a slight clearance at the zero dose position between the drive sleeve locking arm 261 of the drive sleeve 224 and the locking arm 258 of the spindle nut 230 (and as illustrated in FIG. 6).

In a preferred embodiment a master drug compound, such as insulin, contained within a multiple dose, user selectable device could be used with a single use, user replaceable, module that contains a single dose of a secondary medicament and the single dispense interface. When connected to the primary device, the secondary compound is activated/delivered on dispense of the primary compound. Although the present application specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with the invention.

As disclosed herein, the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala (B26) human insulin; Des(B28-B30) human insulin; Des (B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxy-heptadecanoyl)-des(B30) human insulin and B29-N-(ω-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

Exemplary embodiments of the present drug delivery device have been described. Those skilled in the art will understand, however, that changes and modifications may be made to these embodiments without departing from the true scope and spirit of the presently proposed drug delivery device, which is defined by the claims.

TABLE 1

| Dialled Insulin Dose | Pen Number 1 | 2 | 3 | 4 |
|---|---|---|---|---|
| 2 | | | | |
| 4 | | | | |
| 6 | | | | |
| 8 | | | | |
| 10 | | | | |
| 12 | | | | |
| 14 | | | | |
| 16 | | | | |
| 18 | | | | |
| 20 | | | | |
| 22 | | | | |
| 24 | | | | |
| 26 | | | | |
| 28 | | | | |
| 30 | | | | |
| 32 | | | | |
| 34 | | | | |
| 36 | | | | |
| 38 | | | | |
| 40 | | | | |
| 42 | | | | |
| 44 | | | | |
| 46 | | | | |
| 48 | | | | |
| 50 | | | | |
| 52 | | | | |
| 54 | | | | |
| 56 | | | | |
| 58 | | | | |
| 60 | | | | |
| 62 | | | | |
| 64 | | | | |
| 66 | | | | |
| 68 | | | | |
| 70 | | | | |
| 72 | | | | |
| 74 | | | | |
| 76 | | | | |
| 78 | | | | |
| 80 | | | | |

Dose may be dialled and delivered
Low dose - Cannot be dispensed
High dose - Cannot be dialled

TABLE 2

| Dialled Insulin Dose | Pen Number 1 | 2 | 3 | 4 |
|---|---|---|---|---|
| 2 | | | | |
| 4 | | | | |
| 6 | | | | |
| 8 | | | | |
| 10 | | | | |
| 12 | | | | |
| 14 | | | | |
| 16 | | | | |
| 18 | | | | |
| 20 | | | | |
| 22 | | | | |
| 24 | | | | |
| 26 | | | | |
| 28 | | | | |
| 30 | | | | |
| 32 | | | | |
| 34 | | | | |
| 36 | | | | |
| 38 | | | | |
| 40 | | | | |
| 42 | | | | |
| 44 | | | | |
| 46 | | | | |
| 48 | | | | |
| 50 | | | | |
| 52 | | | | |
| 54 | | | | |
| 56 | | | | |
| 58 | | | | |
| 60 | | | | |
| 62 | | | | |
| 64 | | | | |
| 66 | | | | |
| 68 | | | | |
| 70 | | | | |
| 72 | | | | |
| 74 | | | | |
| 76 | | | | |
| 78 | | | | |
| 80 | | | | |

Dose may be dialled and delivered
Low dose - Cannot be dispensed
High dose - Cannot be dialled

TABLE 3

| Dialled Long Acting Insulin Dose | Premix Pen Number 1 | 2 | 3 | 4 | 5 | 6 |
|---|---|---|---|---|---|---|
| | Mix ratio (insulin:GLP-1) | | | | | |
| | 0.83 | 0.665 | 0.53 | 0.43 | 0.35 | 0.285 |
| 2 | | | | | | |
| 4 | | | | | | |
| 6 | | | | | | |
| 8 | | | | | | |
| 10 | | | | | | |
| 12 | | | | | | |
| 14 | | | | | | |
| 16 | | | | | | |
| 18 | | | | | | |
| 20 | | | | | | |
| 22 | 18.3 | | | | | |
| 24 | 19.9 | | | | | |
| 26 | 21.6 | | | | | |
| 28 | | 18.6 | | | | |
| 30 | | 20.0 | | | | |
| 32 | | 21.3 | | | | |
| 34 | | | 18.0 | | | |
| 36 | | | 19.1 | | | |
| 38 | | | 20.1 | | | |
| 40 | | | 21.2 | | | |

TABLE 3-continued

| | | | | | |
|---|---|---|---|---|---|
| 42 | | | | 18.1 | |
| 44 | | | | 18.9 | |
| 46 | | | | 19.8 | |
| 48 | | | | 20.6 | |
| 50 | | | | 21.5 | |
| 52 | | | | | 18.2 |
| 54 | | | | | 18.9 |
| 56 | | | | | 19.6 |
| 58 | | | | | 20.3 |
| 60 | | | | | 21.0 |
| 62 | | | | | 21.7 |
| 64 | | | | | 18.2 |
| 66 | | | | | 18.8 |
| 68 | | | | | 19.4 |
| 70 | | | | | 20.0 |
| 72 | | | | | 20.5 |
| 74 | | | | | 21.1 |
| 76 | | | | | 21.7 |
| 78 | | | | | |
| 80 | | | | | |

GLP-1 Dose - may be dialled and delivered
Low dose - Cannot be dispensed
High dose - Cannot be dialled

The invention claimed is:

1. Dose setting mechanism for a drug delivery device, the mechanism comprising:
    a housing;
    a dose dial component positioned at least partly in the housing, the dose dial component is rotatable during a dose setting step;
    a drive sleeve positioned at least partly within the dose dial component, the drive sleeve is configured to drive a rotatable spindle during a dose administration step;
    a spindle nut coupled to the spindle; and
    a sprung lock nut removably coupled to the drive sleeve and/or to the spindle nut and rotationally fixed to the housing;
    wherein, when the dose dial component is rotated to select a dose greater than a preselected first dose and less than a preselected second dose, the sprung lock nut is decoupled from the spindle nut thus allowing the spindle nut to rotate thereby preventing the selected dose from being administered.

2. Mechanism according to claim 1 wherein, when the dose dial component is rotated to select the dose less than the preselected second dose, the sprung lock nut compresses against a spring, disengages from the spindle nut and allows the spindle nut to rotate.

3. Mechanism according to claim 1 wherein, when the dose dial component is rotated to select a dose greater than the preselected second dose, the sprung lock nut engages the spindle nut and prevents the spindle nut from rotating.

4. Mechanism according to claim 3 wherein, when the dose dial component is rotated to select the dose greater than the preselected second dose, a biasing member forces the sprung lock nut to engage the spindle nut and prevent the spindle nut from rotating.

5. Mechanism according to claim 1 wherein, when the dose dial component is rotated to select the dose less than the preselected second dose, the sprung lock nut acts against a biasing member.

6. Mechanism according to claim 1 wherein the sprung lock nut comprises at least one locking arm, the at least one locking arm releasably coupling the sprung lock nut to the drive sleeve when the dose dial component is rotated to select the dose that is less than the minimum dose.

7. Mechanism according to claim 1 wherein the sprung lock nut is splined to a fixed member, wherein the fixed member is attached to the housing.

8. Mechanism according to claim 1 wherein the dose setting mechanism is a resettable dose setting mechanism.

9. Mechanism according to claim 1 wherein the dose setting mechanism is coupled to a cartridge holder containing a cartridge containing a medicament.

10. Mechanism according to claim 9 wherein the dose setting mechanism is removably coupled to the cartridge holder.

11. Mechanism according to claim 1 wherein the preselected first dose is zero units.

12. Mechanism according to claim 1 wherein the preselected first dose is a priming dose larger than zero units.

13. Mechanism according to claim 12, wherein the preselected first dose is a priming dose of less than about 2 units.

14. Mechanism according to claim 1 wherein, when the dose dial component is rotated to select a dose that is less than the preselected first dose, the sprung lock nut is engaged with the spindle nut and thereby prevents rotation of the spindle nut.

15. A method of setting at least a predetermined minimum dose of a medicament, the method comprising:
    setting a dose by rotating a dose dial component in a first direction relative to a device housing, where the dose dial component is in clutched engagement with a drive sleeve causing the dose dial component and the drive sleeve to move in a proximal axial direction, wherein the drive sleeve is configured to drive a spindle during a dose administration step;
    forcing a sprung lock nut to disengage from a spindle nut when a dose greater than a preselected first dose and less than the predetermined minimum dose, wherein the spindle nut is coupled to the spindle and is axially fixed;
    at a predetermined distance corresponding to the predetermined minimum dose, forcing the sprung lock nut to disengage from the drive sleeve, wherein a biasing member forces the sprung lock nut to re-engage with the spindle nut.

16. The dose setting mechanism of claim 1, wherein the sprung lock nut remains rotationally fixed to the housing during the dose setting step and during the dose administration step.

17. The dose setting mechanism of claim 1, further comprising a biasing member, wherein the sprung lock nut is biased, in an axial direction, by the biasing member.

18. The method of claim 15, wherein the biasing member comprises a spring.

* * * * *